United States Patent
Green

[11] 4,016,750
[45] Apr. 12, 1977

[54] ULTRASONIC IMAGING METHOD AND APPARATUS

[75] Inventor: Philip S. Green, Atherton, Calif.

[73] Assignee: Stanford Research Institute, Menlo Park, Calif.

[22] Filed: Nov. 6, 1975

[21] Appl. No.: 629,594

[52] U.S. Cl. .............................. 73/67.5 R; 128/2 V
[51] Int. Cl.² ...................................... G01N 29/00
[58] Field of Search ....... 73/67, 67.2, 67.7, 67.8 R, 73/67.5 R, 67.9, 71.5 US; 128/2 V, 2.05 Z

[56] References Cited

UNITED STATES PATENTS

| | | | |
|---|---|---|---|
| 3,033,029 | 5/1962 | Weighart | 73/67.8 R |
| 3,276,249 | 10/1966 | King | 73/67.8 R |
| 3,307,408 | 3/1967 | Thomas et al. | 73/67.2 |
| 3,367,173 | 2/1968 | Uphoff | 73/67.8 R |
| 3,453,871 | 7/1969 | Krautkramer | 73/67.8 R |

FOREIGN PATENTS OR APPLICATIONS 796,600  6/1958  United Kingdom ............ 73/67.8 R Primary Examiner—Richard C. Queisser
Assistant Examiner—Stephen A. Kreitman
Attorney, Agent, or Firm—Victor R. Beckman

[57] ABSTRACT

The ultrasonic imaging method and apparatus comprises an ultrasonic wave transducer supplied with recurrent multifrequency energy pulses for pulse insonification of an object under investigation with ultrasonic waves. Resultant echo waves from the object are directed onto the transducer for converting the same to electrical signals which are supplied to a signal processor which includes a variable bandpass filter. One or more of the filter characteristics are varied as a function of depth from which the echo signals are returned for enhanced resolution and signal-to-noise ratio of the received signal. Preferably, the filter is matched to the noise and signal spectra of the system. For A scan and B scan operations wherein reverberated acoustic pulses are derived from a range of depths a time variable filter is employed for time varying operation thereof.

18 Claims, 4 Drawing Figures

ULTRASONIC IMAGING METHOD AND APPARATUS

ORIGIN OF THE INVENTION

The invention described herein was made in the course of work under a contract with the Department of Health, Education and Welfare.

BACKGROUND OF THE INVENTION

This invention relates to ultrasonic imaging method and apparatus and, in particular, to pulse echo method and apparatus wherein short broadband ultrasonic pulses are applied to the object under investigation, travel into the object, and are reflected by boundaries and discontinuities therein to be returned to the transducer. The received echo signals which are derived from different depths within the object are supplied to a suitable display, and the transducer is moved relative to the object to provide for a two-dimensional display. The above-described technique, generally referred to as B-scan, often utilizes a cathode ray tube display in which one of the deflection voltages is proportional to the transducer position, the orthogonal deflection voltage is proportional to the time elapsed since the energizing pulse, and the cathode ray tube beam is modulated by the received pulse intensity. The resulting image is of a section of the object lying in the plane of the propagating ultrasonic waves. A narrow beam is employed which often is focused at an operating depth within the object field for improved lateral resolution.

Such pulse echo method and means of ultrasonic imaging often are employed for imaging of living organisms. Pulses that are reflected from scatterers further within the organism experience greater attenuation, and it is common practice to compensate for such difference in attenuation by time variable gain amplification of the received signal. It will be understood, however, that the attenuation within organs or other tissues varies also with frequency of the ultrasonic wave. In particular, the attenuation coefficient of tissue increases substantially linearly with frequency, with the high frequency spectral components of the returned signal being attenuated more severely than the low frequency components. Typically, the center frequency of the received signal drops in frequency with depth of penetration, first at a moderate rate, then steeply, and finally at a low rate. In brief, not only is the amplitude of the return signal time dependent, but the spectral distribution of the return energy pulse also is time/depth dependent. Prior art echographic ultrasonic imaging system and method typically include time variable gain amplifying means in the signal processing system for increased gain with range to offset the loss of signal strength caused by tissue absorption without provision to compensate for changes in the spectral distribution of the return signal with time, or depth of penetration.

SUMMARY OF THE INVENTION

An object of this invention is the provision of method and apparatus for ultrasonic imaging which overcome the abovementioned shortcomings of prior art arrangements, and which include means to compensate for changes in the spectral distribution of the received signal with changes in range.

An object of this invention is the provision of method and apparatus for ultrasonic imaging which include signal processing means for the received signal which provide for improved resolution and/or signal to noise ratio by use of spectral distribution compensation means.

An object of this invention is the provision of an improved signal processing arrangement for ultrasonic imaging apparatus to compensate for changes in the spectral distribution of the received ultrasonic signal produced by changes in distance traveled within the object under investigation.

Briefly, the above and other objects and advantages are achieved by use, in an ultrasonic imaging system, of signal processing means which includes variable band-pass filter means having one or more filter characteristics which are varied, or controlled, in accordance with the time of travel of the ultrasonic pulse wave within the object under investigation. Controllable band-pass filter characteristics include, for example, filter transmission, bandwidth, and center frequency. For A and B scan methods of ultrasonic examination filter characteristics are time varied in accordance with the depth from which the echo signals are received, and for C scan operation the filter characteristics are adjusted to match the selected range setting. Generally, the filter center frequency, bandwidth and upper, or high, frequency cutoff frequency are reduced with increased operating depth for improved system operation.

The invention will be better understood from the following description taken in connection with the accompanying drawings. In the drawings, wherein like reference characters refer to the same parts in the several views.

Figure 1:
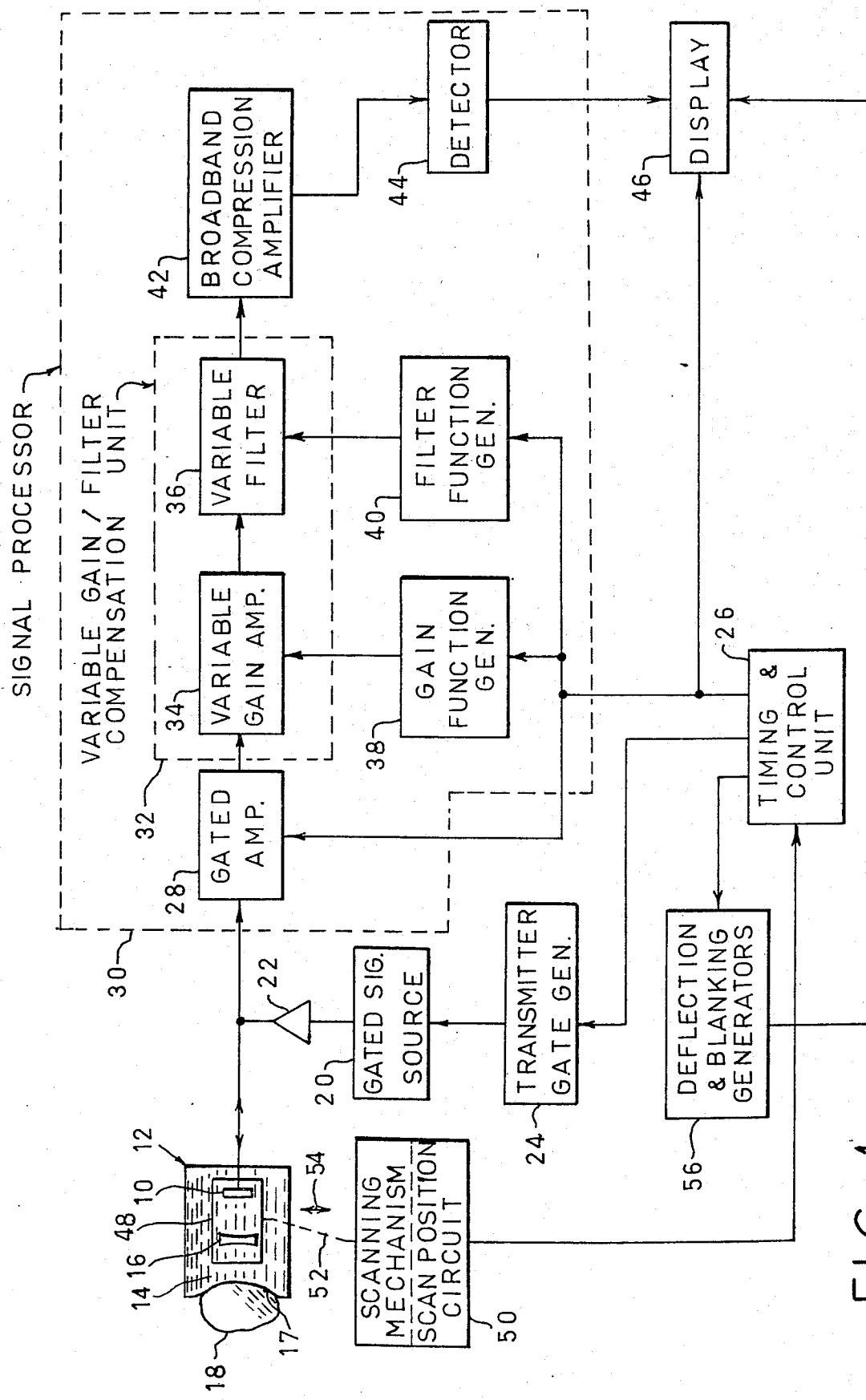
FIG. 1 is a block diagram of a B scan ultrasonic imaging system which includes signal processing means embodying this invention.

Reference first is made to FIG. 1 wherein there is shown an ultrasonic imaging arrangement comprising a transducer 10 which, in the illustrated arrangement is used both for transmitting and receiving ultrasonic pulse signals. For purposes of illustration the transducer is shown immersed in a container 12 containing a suitable acoustic transmission medium 14 such as water for the support of acoustic waves. Ultrasonic compressional wave pulses generated by the transducer 10 are transmitted through an acoustic lens 16 in the fluid medium and coupled through an acoustically transparent window 17 to the subject 18 under investigation for focusing of the pulses within the subject. Such arrangements are well adapted for imaging living organisms such as the heart in a living body, however it will be apparent that the invention is not limited to any such particular application or use. Preferably, a broad band pulse is supplied to the transducer 10 from a gated signal source 20 through a power amplifier 22 for multifrequency pulse insonification of the subject 18. Typically, pulses of ultrasonic waves within the range of, say, 1 to 10 MHz may be employed. The signal source 20 is recurrently gated on as by use of a transmitter gate generator 24 under control of signals from a timing and control unit 26. Periodic pulse operation generally is employed, although aperiodic and continuous wave mode operation may be used. Also, it will be understood that the invention is not limited to use with any particular broad band signal source. For example, broad band operation by use of a short pulse source, or as by use of a pulse or a continuous sweep frequency, frequency modulated (e.g., chirp), random noise, or the like, signal source is contemplated.

Ultrasonic pulses reflected from the boundaries and internal discontinuities of the subject 18 are received by the transducer 10 and the resultant electrical signals are supplied to a gated amplifier 28 which is gated on and off during the receiving and transmitting portions, respectively, of the operating cycle under control of the timing and control unit 26. If desired, a transmit/receive switch, not shown, could be employed in the connection of the transducer 10 to the signal source 20 and signal processor, or receiver, 30, which switch would eliminate the need to gate the amplifier to prevent blocking of the receiver by the transmitter pulses.

In accordance with the present invention the signal processor includes a variable gain/filter compensation unit 32 to which the amplified echo signals are supplied. For purposes of illustration the compensation unit 32 is shown comprising separate variable gain amplifier 34 and variable filter 36 units. As will become apparent hereinbelow the amplifier and filter units simply may be combined in the form of a single variable gain/filter multistage amplifier having the desired variable gain and bandpass filter characteristics.

For use in A and B scan operations, wherein the return signals are received from a range of distances within the subject, the variable gain amplifier and filter means 34 and 36, respectively, are time varied. As noted above the employment of time variable signal amplification in ultrasonic diagnostic systems is well known and includes the use of a variable gain amplifier having a gain which is time varied in accordance with the lapsed time from the last transmitted pulse. In the illustrated arrangement the gain of the variable gain amplifier 34 is varied in accordance with the output from a gain function generator 38, with the timing of the operation of the generator 38 being under control of the timing and control unit 26. Often, the generator 38 simply comprises a ramp generator with an output signal which functions to increase the gain of amplifier 34 in proportion to range in a manner to offset the loss of signal caused by acoustic absorption within the subject. Instead of a fixed function generator, an adjustable function generator may be used whereby a signal of desired shape easily may be obtained for control of amplifier gain. In any case, time variable gain amplification is well known as disclosed, for example, in the publication "Physical Principles of Ultrasonic Diagnosis" - Academic Press, London, England, by P. N. T. Wells, copyright 1969, and no additional description of such operation is believed to be required.

In the illustrated arrangement filter characteristics of the variable filter means 36 are controlled by a filter function generator 40, with timing of the operation of the generator 40 being provided by the timing and control unit 26. For the illustrated B-scan operation the filter transmission factor as a function of frequency of the variable filter 36 is varied as a function of time by output from the filter function generator 40 for improved lateral and longitudinal resolution of the system as well as improved signal to noise ratio in a manner described in detail hereinbelow with reference to FIG. 2. For present purposes it will be seen that the output from the variable gain/filter compensation unit 32 is applied to a broad band compression amplifier 42 comprising, for example, a DC coupled log amplifier with a compression factor of 40 to 60 dB. The amplifier output is detected by an envelope detector 44 comprising, for example, a full wave rectifier with low pass filter means and having as an output a signal which is proportional to the envelope of the broad band high frequency signal output from the amplifier 42. For the illustrated B scan operation, the detector output is supplied to a cathode ray tube display 46 and, in particular, to the control grid thereof to intensity modulate the electron beam. It here will be noted that for A scan operation the detector output simply may be supplied as a deflection signal to a cathode ray tube for deflection of the beam in one direction while a ramp signal synchronized with the transmitter operation is supplied as a deflection signal for deflection of the beam in an orthogonal direction.

For the illustrated B scan operation the transducer 10 and associated focusing lens 16 are moved with a scanning motion relative to the subject 18. In FIG. 1 the transducer and lens are shown mounted on a movable platform 48 connected to a scanning mechanism 50 through a mechanical linkage 52. Linear and/or sector scanning may be employed and for purposes of illustration linear scanning across the object 18 in the direction of the arrow 54 is shown. The scanning mechanism includes a scan position information circuit having an output which is connected to the timing and control unit 26 having outputs for synchronizing the transmitting, receiving and display scanning operations, including the operation of a deflection and blanking generator 56. One output from generator 56 comprises a deflection voltage which is proportional to the transducer position along its scan, and another output which comprises an orthogonal deflection voltage which is proportional to the time elapsed since the last pulse was transmitted. The invention is not limited to use with any particular scanning arrangement. For example, the acoustic wave from the transducer may be deflected to sweep the wave over the object without relative movement of the transducer and object. Also, the use of a transducer array is contemplated in place of the illustrated transducer.

Figure 2:
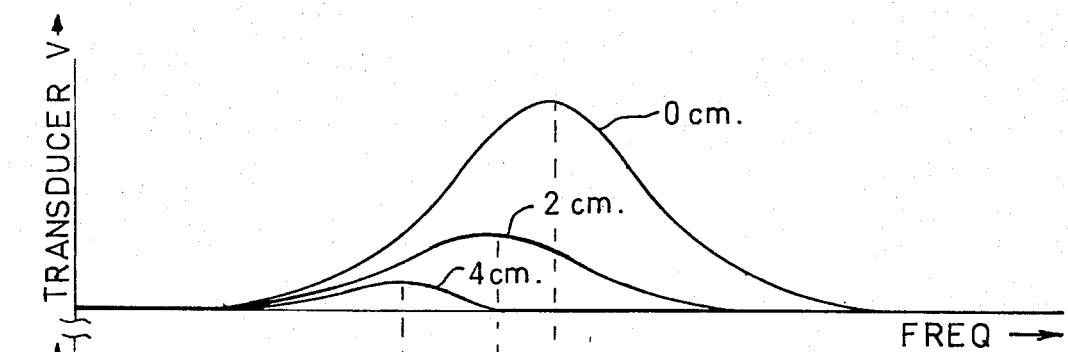
FIG. 2 shows, on a common frequency scale, frequency spectra of return signals obtained from different depths, the return signals after time gain compensation, and curves showing band pass filter transmission factors as a function of frequency for the different depth return signals.
Figure 2:
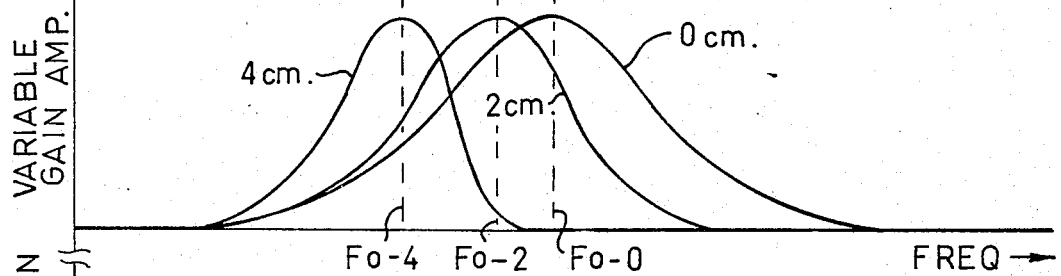
Figure 2:
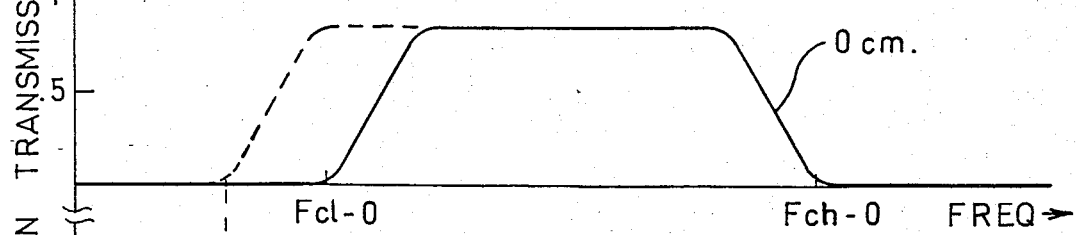
Figure 2:
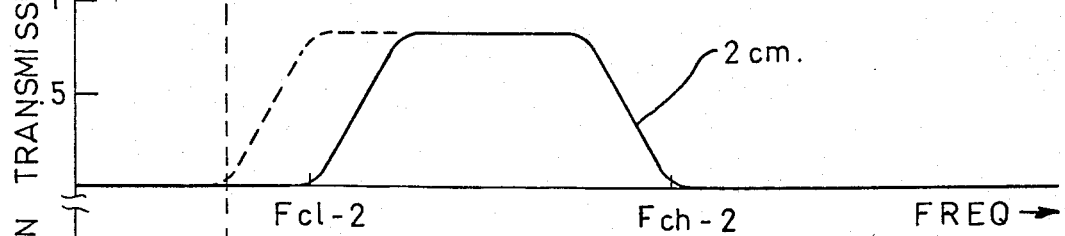
Figure 2:
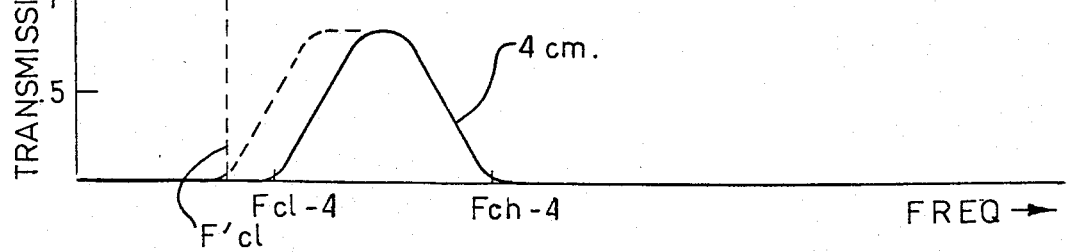

As noted above the attenuation coefficient of tissue comprising the subject 18 increases approximately linearly with frequency such that the high frequency spectral components of the echo signals are attenuated more severely than the low frequency components. Reference is made to FIG. 2 wherein exemplary spectral distribution curves of pulse energy received by the transducer 10 (FIG. 2A) and of the amplified signal from variable gain amplifier 34 (FIG. 2B) are shown for signals received from the adjacent boundary of the subject 18 with the acoustic medium, and for echo signals received from internal discontinuities at 2 and 4 centimeters from the boundary, which curves are labeled 0cm, 2cm, and 4cm, respectively, in FIG. 2. The center frequencies for the echo signals received from the 0cm, 2cm, and 4cm levels are identified on the frequency scale as fo-0, fo-2, and f0-4, respectively. From FIG. 2A it will be seen that the amplitude, bandwidth and center frequency of the received signal decrease with depth of penetration. In practice, the center frequency first drops at a moderate rate, then steeply, and then at a lower rate with increased signal penetration.

The transmission factor versus frequency characteristic of the variable filter 36 is controlled so as to enhance resolution, both lateral and longitudinal, and/or improve signal to noise ratio. As is understood, lateral resolution is proportional to frequency and so improves with increased frequency, and longitudinal resolution is proportional to bandwidth and so improves with increased signal bandwidth. On the other hand, the signal to noise ratio improves with a decrease in the bandwidth. The conflicting requirements for improved operation thereby require tradeoffs in the design and operation of the variable filter 36 and, in practice, the variable filter characteristics are chosen for optimization of operation of the associated ultrasonic imaging system. Obviously, the filter design not only depends upon the frequency and characteristics of the received signals, but depends also upon the nature of the interference, or noise, to be rejected. For present purposes it will be assumed that the noise level is substantially uniform throughout the operating frequency spectrum.

Reference now is made to sections C, D and E of FIG. 2 wherein the filter transmission factor of the variable filter 36 as a function of frequency at the above mentioned. 0, 2 and 4 centimeter depths, respectively, are shown in solid lines. At zero depth the variable filter has a wide transmission band centered substantially at the center frequency fo-0 of the received signal. The low and high frequency cut off frequencies fcl-0 and fch-0 are identified for the 0cm filter transmission factor versus frequency curve of FIG. 2C.

At shallow depths (e.g. at 2cm.) where the center frequency fo-2 of the received signal is reduced, the illustrated filter transmission characteristics are altered so as to reduce the high frequency cutoff frequency to a frequency fch-2. (See FIG. 2D.) The variable filter bandwidth and center frequency also are decreased with the center frequency of the variable filter being shifted downwardly at substantially the same rate as the received signal center frequency fo decreases with depth of penetration.

As penetration increases the received signal decreases such that the signal to noise ration also decreases. Consequently, the filter characteristics become of greater importance at greater operating depths. FIG. 2E shows the filter characteristic for operation at the 4cm depth. There, the filter high frequency cutoff frequency fch-4 is further reduced, the filter center frequency substantially coincides with the center frequency fo-4 of the received signal, and the transmission band is reduced in width for operation with the narrower frequency spectrum of the received signal.

It will be understood that the filter transmission factor versus frequency curves shown at C, D and E of FIG. 2 are for purposes of illustrating operation of one suitable variable filter means, and that the invention is not limited specifically thereto. For example, where the signal to noise ratio is relatively large, at shallow depths, (e.g., at 2cm) the filter may be operated with substantially the same transmission characteristics as exist at the 0cm depth. Thus, although the high frequency spectral components are attenuated more than the low frequency components, at shallow depths it often is advantageous to maintain the high frequency filter transmission since the high frequency operation provides for good lateral and longitudinal, or depth, resolution. Therefore, substantially the same illustrated filter characteristics for operation at 0cm. may be employed at shallow depths to, say 2cm. At increased depths, the characteristics could be varied in the manner described above, wherein the high frequency cutoff frequency decreases with increased depth.

In another modification of the invention the variable filter is provided with a substantially fixed low frequency cutoff frequency fcl identified in FIG. 2, the low frequency end of the variable filter characteristics of such a modified filter being shown in broken lines in sections C, D and E of FIG. 2. The upper frequency end of the filter characters may remain as illustrated in full line. The design of such a filter, wherein only the high frequency cutoff frequency is variable may be simpler than that of a filter in which the low frequency cutoff frequency also is varied. With this arrangement the filter is provided with a low frequency cutoff frequency which best matches the low frequency characteristic of the received frequency spectrum at substantially maximum operating depth, which, in the illustrated arrangement is on the order of six centimeters. Obviously, changes in the filter transmission factor which involve other than the high frequency cutoff frequency, bandwidth and center frequency changes may be employed as desired, or required.

It will be understood that where the echo signal is time variable, as with the illustrated B scan arrangement of FIG. 1 the transmission factor versus frequency characteristic of the filter also is time varied, and that FIG. 2 simply illustrates operation at three specific depths. Often, the particular time varying filter characteristic of any given filter is readily matched to the system response characteristic by the proper selection of waveform output, or outputs, from the filter function generator 40. As noted above, in some instances the signal used to control the variable gain amplifier 34 also may be used for control of the variable filter whereby only a single gain/filter function generator is required.

The prior art includes numerous filter means which exhibit a filter transmission factor versus frequency function which is readily variable, and it will be apparent that the present invention is not limited to the use of any particular type of such variable filter means. There are numerous variations of variable band pass filters of the type which may be employed in the combination of this invention, including both active and passive types. Pi, L and T section filters, and combinations thereof may be utilized. In U.S. Pat. No. 3,192,491 dated June 29, 1965, by Hesselberth et al, there are shown double tuned bandpass filters of the type which may be used, and the teachings and subject matter of the patent specifically are incorporated herein by reference. Also, as noted above, the variable gain and variable filter functions preferably are included in a single multistage unit which includes suitable variable amplifying the filtering means by which the desired signal compensation may be performed. Preferably, the phase characteristics of the variable filter should remain constant over the operating range thereof.

As noted above, for A and B scan operation a time variable filter is employed. Such filters often include voltage variable reactance elements, such as voltage variable capacitors, to which the output from the filter function generator 40 is supplied through suitable high capacitance d-c blocking capacitors and isolating resistors for voltage control of the capacitance thereof. Varactor diodes often are employed for such purposes.

Figure 3:
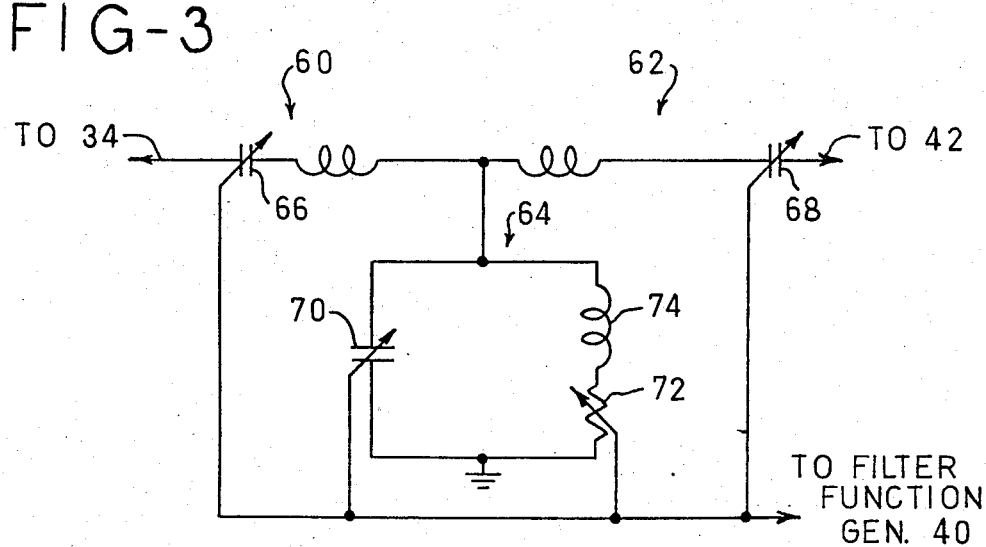
FIG. 3 is a schematic diagram illustrating a prior art type variable filter means which may be employed in the novel signal processing means of this invention shown in FIG. 1.

For purposes of illustration a simplified prior art variable filter circuit is shown in FIG. 3 to which reference now is made. There, a T-section bandpass filter is shown comprising two series LC circuits 60 and 62 in the filter arms and a parallel LC circuit 64 in the leg thereof. The circuits 60, 62 and 64 include variable capacitors 66, 68, and 70, respectively, used for tuning. For operation, the capacitors may be manually variable in accordance with range setting of the imaging system. For the illustrated B scan arrangement wherein the filter transmission factor is time varied, voltage variable capacitor elements, such as varactor diodes may be used for the capacitors 66, 68 and 70. In such case suitable high capacitance d-c blocking capacitors and isolating resistors, not shown, are included in the connection of the filter function generator to the varactor diodes for voltage control of diode capacitance. With such an arrangement the generator output may supply a control voltage for the simultaneous increase of the capacitance of capacitors 66, 68 and 70 with time during the receiving portion of the cycle to reduce the filter center frequency accordingly. Simultaneous bandwidth control of the simplified filter is shown provided by means of a variable resistor 72 in series circuit with inductor 74 in the parallel resonant circuit 64, the value of which is decreased with time during the receiving portion of the cycle. As the resistance decreases the slope of the filter transmission function increases to effectively decrease the filter pass band. The variable resistor 72 may comprise, for example, a field effect transistor which functions as a voltage controlled resistor with the gate thereof connected to the output from the filter function generator 40 for control of the resistance thereof. The showing of the prior art simplified variable filter means of FIG. 3 simply is to facilitate an understanding of the novel signal processing means of the illustrated ultrasonic diagnostic apparatus which includes variable filter means. The actual filter employed would be tailored to the operating characteristics of the system and, as noted above easily may be included in the conventional variable gain amplifier means.

Figure 4:
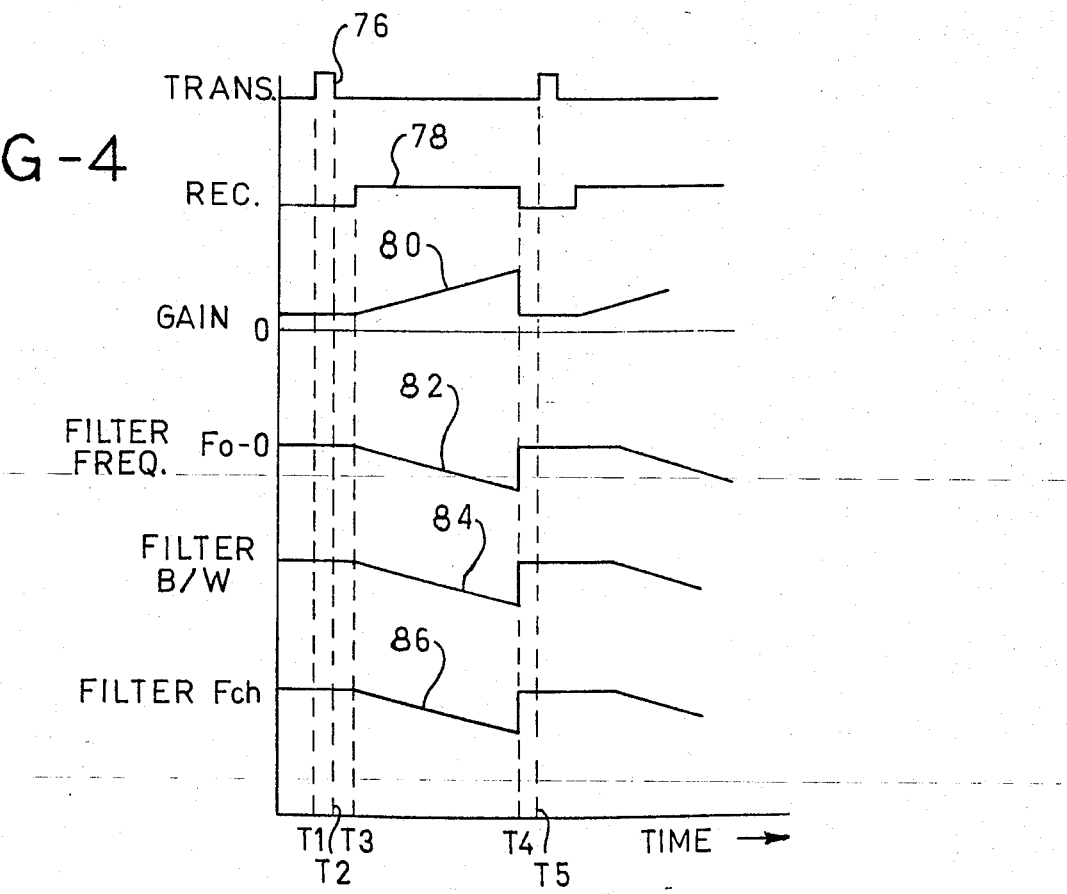
FIG. 4 is a timing diagram for use in explaining the operation of the ultrasonic imaging apparatus shown in FIG. 1.

Although the operation of the ultrasonic diagnostic apparatus of this invention is believed to be apparent from the above description, a brief description thereof with reference to the timing diagram of FIG. 4 now will be made. The transducer 10 and lens 16 are moved across the object 18 in the direction of the arrow 54 by the scanning mechanism 50. A scan position signal is produced by the scan position circuit of the scanning mechanism and supplied to the timing and control unit 26 from which control signals for timing the operation of the transmitter, receiver, and cathode ray tube scanning means are obtained. Broadband narrow beam ultrasonic waves are generated during the transmit pulse period 76 shown in FIG. 4, which pulse is initiated at time T1 and is terminated at time T2. The pulse travels through the lens 16 and into the subject 18 to be reflected at the boundary of the subject with the fluid 14 and from different levels at discontinuities within the subject. After a time delay period, between times T2 and T3, the receiver is gated on for processing the echo signals as shown at 78. During operation of the receiver between times T3 and T4 the gain of the variable gain amplifier 34 is increased as indicated by gain curve 80 of FIG. 4 for increased amplification of the echo signals received from a greater depth within the subject in the well known manner. In accordance with the present invention, during the receiver operation the transmission factor of the variable filter 36 is controlled for enhanced resolution and/or signal to noise ratio.

Here, for purposes of illustration, at time T3 the filter center frequency, curve 82, is shown decreasing with time from fo-0 to substantially match, or follow, the decrease in the echo signal center frequency with depth of penetration. Simultaneously, the filter bandwidth, curve 84, and filter high frequency cutoff frequency, curve 86, are decreased with time to better fit the bandwidth of the echo signal for improved signal to noise ratio. At time T4 the receiving operation is terminated, another transmitter pulse is initiated at time T5, and the above described operating cycle is repeated.

The invention having been described in detail in accordance with the requirements of the Patent Statutes various other changes and modifications will suggest themselves to those skilled in this art, and it is intended that such changes shall fall within the spirit and scope of the invention as defined in the appended claims.

I claim:

1. In an ultrasonic system for the examination of the interior of objects, such as body parts, the combination comprising,
   means for insonification of an object under examination with a broadband ultrasonic wave signal,
   means for receiving echo signals from discontinuities over a range of depths within the insonified object and for converting the same to electrical signals,
   means for filtering said electrical signals by bandpass filter means having a filter transmission factor as a function of frequency which is variable, and
   means for compensating for depth dependent changes in the spectral distribution of the echo signals by time varying the filter transmission factor versus frequency characteristic of the bandpass filter means in accordance with the depth of the discontinuity from which the echo signal is reflected.

2. In an ultrasonic system as defined in claim 1 wherein,
   said means for insonification of an object under examination comprises means for recurrent pulse insonification of the object, and
   said means for compensating for depth dependent changes in the spectral distribution of the echo signals is recurrently operated for recurrently time varying the filter transmission factor versus frequency characteristic of the bandpass filter means in accordance with the time lapsed from the preceding pulse insonification of the object.

3. In an ultrasonic system as defined in claim 1 wherein the passband of the bandpass filter means is time varied by said means for compensating for depth dependent changes in the spectral distribution of the echo signals by time varying the filter transmission factor versus frequency characteristic of the bandpass filter while receiving the echo signals.

4. In an ultrasonic system as defined in claim 1 wherein the center frequency of the bandpass filter means is time varied by said means for compensating for depth dependent changes in the spectral distribution of the echo signals by time varying the filter transmission factor versus frequency characteristic of the bandpass filter while receiving the echo signals.

5. In an ultrasonic system as defined in claim 4 wherein the passband of the bandpass filter means is simultaneously time varied with the center frequency thereof.

6. In an ultrasonic system as defined in claim 1 wherein the high frequency cutoff frequency of the bandpass filter means is time varied by said means for compensating for depth dependent changes in the spectral distribution of the echo signals by time varying the filter transmission factor versus frequency characteristic of the bandpass filter while receiving the echo signals.

7. In an ultrasonic system as defined in claim 1 including envelope detecting means for envelope detection of the filtered electrical signals, and means for displaying the detected signals.

8. In an ultrasonic system as defined in claim 7 wherein said display means includes a cathode ray tube for B-scan display of the detected signals, said means for insonification of an object under examination includes means for recurrent pulse insonification of the object, and wherein the filter transmission factor versus frequency characteristic of the bandpass filter is time varied and the cathode ray tube beam is deflected in one direction in accordance with the time elapsed from the preceding pulse operation of the insonification means, and including means for relatively sweeping ultrasonic waves produced by the insonification means and the insonified object in a scanning motion, and means for deflecting the cathode ray tube beam in an orthogonal direction in synchronization with said scanning motion of the ultrasonic waves relative to the insonified object.

9. In a method for the non-invasive examination of objects such as body parts, the steps of insonifying at least a portion of the body part with a beam of broadband acoustic energy to produce echo signals from within the body, receiving echo signals from within the body and converting the same to electrical signals, passing the electrical signals through bandpass filter means having a variable filter transmission factor versus frequency characteristic, and time varying the filter transmission factor versus frequency characteristic of the bandpass filter in relationship with the depth from which the echo signals are received while receiving echo signals from over a range of depths within the body for compensating for depth dependent changes in the spectral distribution of echo signals.

10. In a method for the non-invasive examination of objects as defined in claim 9 wherein the filter transmission factor versus frequency characteristic of the bandpass filter which is time varied comprises the filter passband which is reduced as the depth from which the echo signals are received is increased.

11. In a method for the non-invasive examination of objects as defined in claim 9 wherein the filter transmission factor versus frequency characteristic of the bandpass filter which is time varied comprises the filter center frequency which is reduced as the depth from which the echo signals are received is increased.

12. In a method for the non-invasive examination of objects as defined in claim 11 wherein the passband of the bandpass filter simultaneously is reduced as the filter center frequency is reduced.

13. In a method for the non-invasive examination of objects as defined in claim 9 wherein the insonifying step includes recurrently insonifying with broadband acoustic energy pulses, and the receiving step recurrently is effected after said pulse insonification.

14. In a method for the non-invasive examination of objects as defined in claim 9 wherein the step of time varying the filter transmission factor versus frequency characteristic of the bandpass filter means comprises reducing the high frequency cutoff frequency of the filter means as the depth from which the echo signals are received increases.

15. In an ultrasonic system for the examination of the interior body parts, or the like, the combination comprising, means for recurrent pulse insonification of a body part under examination, means for receiving echo signals from discontinuities within said body part over a time period following pulse insonification, which signals have a spectral distribution dependent upon the depth within the body part from which the signal is received, and for converting received echo signals to electrical signals, bandpass filter means having variable operating characteristics through which said electrical signals are passed, and means for time varying operating characteristics of the bandpass filter means while passing said electrical signals therethrough for relating filter operating characteristics with the time varying spectral distribution of the electrical signal.

16. In a method for the non-invasive examination of the interior of objects such as living organisms, or the like, the steps of, pulse insonifying at least a portion of an object to be examined with an acoustic energy beam to produce echo signals from discontinuities within the object, receiving over a time period following said pulse insonifying step echo signals from within the body, which echo signals have a spectral distribution dependent upon the depth from which the signal is received, converting the received echo signals to electrical signals, passing the electrical signals through bandpass filter means having a variable filter transmission factor versus frequency characteristic, and time varying the filter transmission factor versus frequency characteristic of said bandpass filter means while the electrical signals are passed therethrough to match the variable filter transmission factor versus frequency characteristic of said bandpass filter means with the time varying spectral distribution of the electrical signal for improving the signal to noise ratio of the electrical signals.

17. In a pulse operated ultrasonic imaging apparatus of the type which includes ultrasonic wave transducer means for transmitting ultrasonic wave pulses into an object to be examined and for converting reflected ultrasonic waves received over a range of depths therewithin into an electrical signal, the spectral distribution of said reflected ultrasonic waves being dependent upon the depth from which they are received, a receiver for processing said electrical signal, said receiver including time variable filter means, and means for time varying said time variable filter means while processing said electrical signal produced by ultrasonic waves received from over a range of depths to compensate for changes in the spectral distribution of the reflected ultrasonic waves with depth.

18. In an ultrasonic imaging apparatus of the type defined in claim 17 wherein said transducer means produces ultrasonic wave beams with said pulse operation thereof, means for scanning said ultrasonic wave beam within said object, visual display means responsive to the output from the receiver for displaying a B-scan image of a section of the object, and means for generating timing pulses representative of the scanning position of the beam for timing operation of the transmitter, the time variable filter means, and the visual display means.

* * * * *

REEXAMINATION CERTIFICATE (196th)
United States Patent [19]
Green

[11] B1 4,016,750

[45] Certificate Issued May 22, 1984

[54] ULTRASONIC IMAGING METHOD AND APPARATUS

[75] Inventor: Philip S. Green, Atherton, Calif.

[73] Assignee: Stanford Research Institute, Menlo Park, Calif.

Reexamination Request:
No. 90/000,351, Mar. 24, 1983

Reexamination Certificate for:
Patent No.: 4,016,750
Issued: Apr. 12, 1977
Appl. No.: 629,594
Filed: Nov. 6, 1975

[51] Int. Cl.$^3$ .............................................. G01N 29/00
[52] U.S. Cl. ....................................... 73/629; 73/620; 73/631

[56] References Cited
U.S. PATENT DOCUMENTS
3,309,914  3/1967  Weighart ............................ 73/631

*Primary Examiner*—Stephen A. Kreitman

[57] ABSTRACT

The ultrasonic imaging method and apparatus comprises an ultrasonic wave transducer supplied with recurrent multifrequency energy pulses for pulse insonification of an object under investigation with ultrasonic waves. Resultant echo waves from the object are directed onto the transducer for converting the same to electrical signals which are supplied to a signal processor which includes a variable bandpass filter. One or more of the filter characteristics are varied as a function of depth from which the echo signals are returned for enhanced resolution and signal-to-noise ratio of the received signal. Preferably, the filter is matched to the noise and signal spectra of the system. For A scan and B scan operations wherein reverberated acoustic pulses are derived from a range of depths a time variable filter is employed for time varying operation thereof.

B1 4,016,750

REEXAMINATION CERTIFICATE ISSUED UNDER 35 U.S.C. 307.

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–6, 9–12, and 14–17 are determined to be patentable as amended:

Claims 7, 8, 13 and 18, dependent on amended claims, are determined to be patentable.

New claims 19–20 are added and determined to be patentable.

1. In an ultrasonic system for the examination of the interior of objects, such as body parts, the combination comprising,
    means for insonification of an object under examination with a broadband ultrasonic wave signal,
    means for receiving echo signals from discontinuities over a range of depths within the insonified object and for converting the same to electrical signals,
    means for filtering said electrical signals by bandpass filter means having a [filter transmission factor as a function of frequency which is] *continuously variable, unitary, passband*, and
    means for compensating for depth dependent changes in the spectral distribution of the echo signals by time varying [the filter transmission factor versus frequency characteristic] *said unitary passband* of the bandpass filter means in accordance with the depth of the discontinuity from which the echo signal is reflected *while receiving the echo signals*.

2. In an ultrasonic system as defined in claim 1 wherein,
    said means for insonification of an object under examination comprises means for recurrent pulse insonification of the object, and
    said means for compensating for depth dependent changes in the spectral distribution of the echo signals is recurrently operated for recurrently time varying the [filter transmission factor versus frequency characteristic] *unitary passband* of the bandpass filter means in accordance with the time lapsed from the preceding pulse insonification of the object.

3. In an ultrasonic system as defined in claim 1 wherein the *unitary* passband of the bandpass filter means is [time varied by said means for compensating for depth dependent changes in the spectral distribution of the echo signals by time varying the filter transmission factor versus frequency characteristic of the bandpass filter while receiving the echo signals] *reduced as the depth from which the echo signals are received increases*.

4. In an ultrasonic system as defined in claim 1 wherein the center frequency of the bandpass filter means is *simultaneously* time varied *with the unitary passband thereof* by said [means for] compensating *means* [for depth dependent changes in the spectral distribution of the echo signals by time varying the filter transmission factor versus frequency characteristic of the bandpass filter] *while receiving the echo signals*.

5. In an ultrasonic system as defined in claim 4 wherein the *unitary* passband *and center frequency* of the bandpass filter means [is] *are* simultaneously [time varied with the center frequency thereof] *reduced as the depth from which the echo signals are received increases*.

6. In an ultrasonic system as defined in claim 1 wherein the high frequency cutoff frequency of the bandpass filter means is *simultaneously* time varied *with the unitary passband thereof* by said [means for] compensating *means* [for depth dependent changes in the spectral distribution of the echo signals by time varying the filter transmission factor versus frequency characteristic of the bandpass filter] *while receiving the echo signals*.

9. In a method for the non-invasive examination of objects such as body parts, the steps of
    insonifying at least a portion of the body part with a beam of broadband acoustic energy to produce echo signals from within the body,
    receiving echo signals from within the body and converting the same to electrical signals,
    passing the electrical signals through bandpass filter means having a *unitary, continuously* variable, [filter transmission factor versus frequency characteristic] *passband*, and
    time varying the [filter transmission factor versus frequency characteristic] *unitary passband* of the bandpass filter in relationship with the depth from which echo signals are received while receiving echo signals from over a range of depths within the body for compensating for depth dependent changes in the spectral distribution of echo signals.

10. In a method for the non-invasive examination of objects as defined in claim 9 wherein the [filter transmission factor versus frequency characteristic of the bandpass filter which is time varied comprises the] filter passband [which] is reduced as the depth from which the echo signals are received is increased.

11. In a method for the non-invasive examination of objects as defined in claim *10* [9 wherein the filter transmission factor versus frequency characteristic of the bandpass filter which is time varied comprises the filter] *including time varying* the center frequency [which is reduced] *of the bandpass filter means as the* [depth from which the] echo signals are received [is increased].

12. In a method for the non-invasive examination of objects as defined in claim 11 wherein the [passband] *center frequency* of the bandpass filter simultaneously is reduced as the filter [center frequency] *passband* is reduced.

14. In a method for the non-invasive examination of objects as defined in claim 9 [wherein the step of time varying the filter transmission factor versus frequency characteristic of the bandpass filter means comprises] *which includes substantially continuously* reducing the high frequency cutoff frequency of the filter means as the depth from which the echo signals are received increases.

15. In an ultrasonic system for the examination of the interior of body parts, or the like, the combination comprising, means for recurrent pulse insonification of a body part under examination, means for receiving echo signals from discontinuities within said body part over a time period following pulse insonification, which signals have a spectral distribution dependent upon the depth within the body part from which the signal is received, and for converting received echo signals to electrical signals, bandpass filter means having *a unitary, continuously* variable [operating characteristics], *passband* through which said electrical signals are passed, and means for time varying [operating characteristics] *the unitary passband* of the bandpass filter means while passing said electrical signals therethrough for relating *the filter* [operating characteristics] *passband* with the time varying spectral distribution of the electrical signal.

16. In a method for the non-invasive examination of the interior of objects such as living organisms, or the like, the steps of, pulse insonifying at least a portion of an object to be examined with an acoustic energy beam to produce echo signals from discontinuities within the object, receiving over a time period following said pulse insonifying step echo signals from within the body, which echo signals have a spectral distribution dependent upon the depth from which the signal is received, converting the received echo signals to electrical signals, passing the electrical signals through bandpass filter means having a *unitary, continuously* variable [filter transmission factor versus frequency characteristic], *passband*, and time varying the [filter transmission factor versus frequency characteristic] *passband of said bandpass filter means* while the electrical signals are passed therethrough to match the variable [filter transmission factor versus frequency characteristic] *passband* of said bandpass filter means with the time varying spectral distribution of the electrical signal for improving the signal to noise ratio of the electrical signals *over the range of depths of operation*.

17. In a pulse operated ultrasonic imaging apparatus of the type which includes ultrasonic wave transducer means for transmitting ultrasonic wave pulses into an object to be examined and for converting reflected ultrasonic waves received over a range of depths therewithin into an electrical signal, the spectral distribution of said reflected ultrasonic waves being dependent upon the depth from which they are received, a receiver for processing said electrical signal, said receiver including time variable filter means *having a unitary passband which is continuously variable,* and means for time varying *the unitary passband of* said time variable filter means while processing said electrical signal produced by ultrasonic waves received from over a range of depths to compensate for changes in the spectral distribution of the reflected ultrasonic waves with depth.

*19. In an ultrasonic system as defined in claim 6 wherein the passband and high frequency cutoff frequency of the bandpass filter means are simultaneously reduced as the depth from which echo signals are received increases.*

*20. In a method for the non-invasive examination of objects such as body parts, the steps of*

*insonifying at least a portion of the body part with a beam of broadband acoustic energy to produce echo signals from within the body,*

*receiving echo signals from within the body and converting the same to electrical signals,*

*passing the electrical signals through bandpass filter means having a variable filter transmission factor versus frequency characteristic, and*

*time varying the filter transmission factor versus frequency characteristic of the bandpass filter in relationship with the depth from which the echo signals are received while receiving echo signals from over a range of depths within the body for compensating for depth dependent changes in the spectral distribution of echo signals, the filter transmission factor versus frequency characteristic of the bandpass filter which is time varied comprising the filter passband which is reduced as the depth from which the echo signals are received is increased.*

* * * * *

REEXAMINATION CERTIFICATE (2264th)

United States Patent [19]
Green

[11] B1 4,016,750
[45] Certificate Issued Apr. 5, 1994

[54] ULTRASONIC IMAGING METHOD AND APPARATUS

[75] Inventor: Philip S. Green, Atherton, Calif.

[73] Assignee: Stanford Research Institute, Menlo Park, Calif.

Reexamination Requests:
No. 90/002,917, Dec. 16, 1992
No. 90/002,936, Jan. 26, 1993
No. 90/002,959, Jan. 29, 1993
No. 90/003,133, Jul. 20, 1993

Reexamination Certificate for:
Patent No.: 4,016,750
Issued: Apr. 12, 1977
Appl. No.: 629,594
Filed: Nov. 6, 1975

[51] Int. Cl.$^5$ ............................................. G01N 29/00
[52] U.S. Cl. ....................................... 73/629; 73/620; 73/631

[56] References Cited

U.S. PATENT DOCUMENTS

| | | |
|---|---|---|
| 2,590,822 | 3/1952 | Minton .................................. 333/18 |
| 2,835,746 | 5/1958 | Montgomery . |
| 3,292,143 | 12/1966 | Russell . |
| 3,364,462 | 1/1968 | Bogs et al. . |
| 3,454,924 | 7/1969 | Sherwood et al. . |
| 3,585,848 | 6/1971 | Korpel . |
| 3,629,796 | 12/1971 | Brownscombe et al. . |

OTHER PUBLICATIONS

*Acoustical Holography*, vol. 5 (ed. Philip S. Green). Title page and preface no date.
Busser, J. H., Executive Director, Alliance for Engineering in Medicine and Biology, Suite 1350, 5454 Wisconsin Avenue, Chevy Chase, Maryland, 20015, technical report entitled "A 5-Year Research and Development Agendum for Ultrasonic Imaging Diagnostic Instrumentation: Final Report of AEMB Task Groups on Ultrasonic Imaging Diagnostic Instrumentation" (Apr. 1975), pp. 3-6, 77-78, 91-108.
Suzuki, T., et al., "Receiving Radar Wave by Time Varying Band Amplifier" *National Academic Conference of Electronic Communications*, Part 3, pp. 105-106. (A 4 page English Translation is also included).
Clay, C. S., *Elementary Exploration Seismology* (1990) Prentice Hall, Inc., New Jersey, Unit 1, pp. 2-4.
McGraw-Hill, *Encyclopedia of Science & Technology* (1987) 6th Edition, vol. 16, pp. 217-220.
Claerbout, J. F., *Imaging the Earth's Interior* (1985) Blackwell Scientific Publications, Oxford, pp. xi-xii.
Coffeen, J. A. *Seismic Exploration Fundamentals* (1978) Petroleum Publishing Company, Oklahoma, Chapter 1, pp. 1-2.
Heiland, C. A. *Geophysical Exploration* (1946) Prentice-Hall, Inc., New York, Chapter 2, pp. 21-23, Chapter 9, pp. 570-571 and 576-579.
Winter, T. C., "A Survey of Sound Propagation in Soils" *Acoustical Holography*, (Green, P. S., Ed.), (1974) Plenum Press, New York, vol. 5, pp. 197-216.
McQuillin, R., et al., *An Introduction to Seismic Interpretation* (1979) Graham & Trotman Limited, London, Chapter 2, p. 9.

*Primary Examiner*—John E. Chapman

[57] ABSTRACT

The ultrasonic imaging method and apparatus comprises an ultrasonic wave transducer supplied with recurrent multifrequency energy pulses for pulse insonification of an object under investigation with ultrasonic waves. Resultant echo waves from the object are directed onto the transducer for converting the same to electrical signals which are supplied to a signal processor which includes a variable bandpass filter. One or more of the filter characteristics are varied as a function of depth from which the echo signals are returned for enhanced resolution and signal-to-noise ratio of the received signal. Preferably, the filter is matched to the noise and signal spectra of the system. For A scan and B scan operations wherein reverberated acoustic pulses are derived from a range of depths a time variable filter is employed for time varying operation thereof.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; Matter printed in italics indicates additions make to the patent.

AS A RESULT OF REEXAMINATION, IT HAS BEEN DETERMINED THAT:

The patentability of claims 17 and 18 is confirmed.

Claims 1, 3, 5, 9-16 and 20 are determined to be patentable as amended.

Claims 2, 4, 6-8 and 19, dependent on an amended claim, are determined to be patentable.

1. In an ultrasonic system for the examination of the interior of objects, [such as body parts,] the combination comprising,
   means for insonification of an object under examination with a broadband ultrasonic wave signal,
   means for receiving echo signals from discontinuities over a range of depths within the insonified object and for converting the same to electrical signals,
   means for filtering said electrical signals by bandpass filter means having a continuously variable, unitary, passband, and
   means for compensating for depth dependent changes in the spectral distribution of the echo signals by time varying said unitary passband of the bandpass filter means in accordance with the depth of the discontinuity from which the echo signal is reflected while receiving the echo signals.

3. In an ultrasonic system as defined in claim 1 wherein the *width of the* unitary passband of the bandpass filter means is reduced as the depth from which the echo signals are received increases.

5. In an ultrasonic system as defined in claim 4 wherein the *width of the* unitary passband and center frequency of the bandpass filter means are simultaneously reduced as the depth from which the echo signals are received increases.

9. In a method for the non-invasive examination of [objects such as] body parts, the steps of
   insonifying at least a portion of the body part with a beam of broadband acoustic energy to produce echo signals from within the body,
   receiving echo signals from within the body and converting the same to electrical signals,
   passing the electrical signals through bandpass filter-means having a unitary, continuously variable, passband, and
   time varying the unitary passband of the bandpass filter in relationship with the depth from which echo signals are received while receiving echo signals from over a range of depths within the body for compensating for depth dependent changes in the spectral distribution of echo signals.

10. In a method for the non-invasive examination of [objects] *body parts* as defined in claim 9 wherein the filter passband is reduced as the depth from which the echo signals are received as the depth from which the echo signals are received is increases.

11. In a method for the non-invasive examination of [objects] *body parts* as defined in claim 10 including time varying the center frequency of the bandpassfilter means as the echo signals are received.

12. In a method for the non-invasive examination of [objects] *body parts* as defined in claim 11 wherein the center frequency of the bandpass filter simultaneously is reduced as the filter passband is reduced.

13. In a method for the non-invasive examination of [objects] *body parts* as defined in claim 9 wherein the insonifying step includes recurrently insonifying with broadband acoustic energy pulses, and the receiving step recurrently is effected after said pulse insonification.

14. In a method for the non-invasive examination of [objects] *body parts* as defined in claim 9 which includes substantially continuously reducing the high frequency cutoff frequency of the filter means as the depth from which the echo signals are received increases.

15. In [an ultrasonic] *a* system for the examination of the interior of body parts, [or the like,] the combination comprising,
   means for recurrent *ultrasonic* pulse insonification of a body part under examination,
   means for receiving echo signals from discontinuities with said body part over a time period following pulse insonification, which signals have a spectral distribution dependent upon the depth within the body part from which the signal is received, and for converting received echo signals to electrical signals,
   bandpass filter means having a unitary, continuously variable passband through which said electrical signals are passed, and
   means for time varying the unitary passband of the bandpass filter means while passing said electrical signals therethrough for relating the filter passband with the time varying spectral distribution of the electrical signal.

16. In a method for the non-invasive examination of the interior of [objects such as] *a* living [organisms or the like] *organism*, the steps of,
   pulse insonifying at least a portion of [an object] *the living organism* to be examined with an acoustic energy beam to produce echo signals from discontinuities within the [object] *organism*,
   receiving over a time period following said pulse insonifying step echo signals from within the [body] *organism*, which echo signals have a spectral distribution dependent upon the depth from which the signal is received,
   converting the received echo signals to electrical signals,
   passing the electrical signals through bandpass filter means having a unitary, continuously variable, passband, and
   time varying the passband of said bandpass filter means while the electrical signals are passed therethrough to match the variable passband of said handpass filter means with the time varying spectral distribution of the electrical signal for improving the signal to noise ratio of the electrical signals over the range of depths of operation.

20. In a method for the non-invasive examination of [objects such as] body parts, the steps of
  insonifying at least a portion of the body part with a beam of broadband acoustic energy to produce echo signals from within the body,
  receiving echo signals from within the body and converting the same to electrical signals,
  passing the electrical signals through bandpass filter means having a variable filter transmission factor versus frequency characteristic, and
  time varying the filter transmission factor versus frequency characteristic of the bandpass filter in relationship with the depth from which the echo signals are received while receiving echo signals from over a range of depths within the body for compensating for depth dependent changes in the spectral distribution of echo signals, the filter transmission factor versus frequency characteristic of the bandpass filter which is time varied comprising the filter passband which is reduced as the depth from which the echo signals are received is increased.

* * * * *